(12) United States Patent
Mower

(10) Patent No.: US 7,722,902 B2
(45) Date of Patent: *May 25, 2010

(54) SOLID DOSAGE FORM FOR PROVIDING A DIETARY SUPPLEMENT

(75) Inventor: Thomas E. Mower, Payson, UT (US)

(73) Assignee: Sakura Properties, LLC, Salem, UT (US)

( * ) Notice: Subject to any disclaimer, the term of this patent is extended or adjusted under 35 U.S.C. 154(b) by 1058 days.

This patent is subject to a terminal disclaimer.

(21) Appl. No.: 11/307,029

(22) Filed: Jan. 19, 2006

(65) Prior Publication Data

US 2006/0210621 A1    Sep. 21, 2006

Related U.S. Application Data

(62) Division of application No. 11/083,826, filed on Mar. 18, 2005.

(51) Int. Cl.
*A01N 65/00*    (2009.01)

(52) U.S. Cl. ..................................................... 424/725

(58) Field of Classification Search ........................ None
See application file for complete search history.

(56) References Cited

U.S. PATENT DOCUMENTS

| | | | |
|---|---|---|---|
| 1,607,844 A | 11/1926 | Neilsen | |
| 1,687,625 A | 10/1928 | Mackenzie | |
| 2,933,431 A | 4/1960 | Sperouleas | |
| 3,240,775 A | 3/1966 | Schweiger | |
| 3,264,188 A | 8/1966 | Gresham | |
| 3,301,746 A | 1/1967 | Sanford | |
| 3,697,287 A | 10/1972 | Wintz | |
| 3,700,623 A | 10/1972 | Keim | |
| 3,741,273 A | 6/1973 | Meade | |
| 3,772,076 A | 11/1973 | Keim | |
| 3,911,105 A | 10/1975 | Papantoniou et al. | |
| 4,009,313 A | 2/1977 | Crawford | |
| 4,112,167 A | 9/1978 | Dake | |
| 4,139,619 A | 2/1979 | Chidsey | |
| 4,481,243 A | 11/1984 | Allen | |
| 4,556,560 A | 12/1985 | Buckingham | |
| 4,596,812 A | 6/1986 | Chidsey | |
| 4,670,285 A | 6/1987 | Clandinin | |
| 4,698,360 A | 10/1987 | Masquelier | |
| 4,871,550 A | 10/1989 | Millman | |
| 4,996,044 A | 2/1991 | Mercado | |
| 4,996,238 A | 2/1991 | Matravers | |
| 5,021,245 A | 6/1991 | Borschel | |
| 5,059,686 A | 10/1991 | Sau | |
| 5,152,983 A | 10/1992 | Nambudiry | |
| 5,165,933 A | 11/1992 | Oishi | |
| 5,292,538 A | 3/1994 | Paul | |
| 5,362,488 A | 11/1994 | Sibley | |
| 5,397,786 A | 3/1995 | Simone | |
| 5,409,703 A | 4/1995 | McAnalley | |
| 5,415,879 A | 5/1995 | Oh | |
| 5,541,166 A | 7/1996 | Parish et al. | |
| 5,631,032 A | 5/1997 | Gil | |
| 5,672,339 A | 9/1997 | Soyama et al. | |
| 5,700,590 A | 12/1997 | Masor | |
| 5,720,966 A | 2/1998 | Ostendorf | |
| 5,733,572 A | 3/1998 | Unger | |
| 5,762,945 A | 6/1998 | Ashley | |
| 5,776,494 A | 7/1998 | Guskey | |
| 5,814,188 A | 9/1998 | Vinson | |
| 5,834,044 A | 11/1998 | Schmitz | |
| 5,861,048 A | 1/1999 | Kamasaka | |
| 5,891,888 A | 4/1999 | Strahl | |
| 5,980,922 A | 11/1999 | Mackey | |
| 6,033,887 A | 3/2000 | Charpentier | |
| 6,051,235 A | 4/2000 | Theuer | |
| 6,051,236 A | 4/2000 | Portman | |
| 6,077,557 A | 6/2000 | Gordon et al. | |
| 6,190,724 B1 | 2/2001 | Sawatzki et al. | |
| 6,268,182 B1 | 7/2001 | Kamasaka et al. | |
| 6,346,237 B2 | 2/2002 | Lemann et al. | |
| 6,447,817 B1 | 9/2002 | Niyiro | |
| 6,517,849 B1 | 2/2003 | Seger et al. | |

(Continued)

FOREIGN PATENT DOCUMENTS

EP    1199942    5/2002

(Continued)

OTHER PUBLICATIONS

Spice Pages, 11 pages, 2009.*

(Continued)

*Primary Examiner*—Michael V Meller
(74) *Attorney, Agent, or Firm*—Clayton, Howarth & Cannon, P.C.

(57) ABSTRACT

Compositions and methods relating to partially hydrolyzed fucoidan for use in dietary supplements are described. Fucoidan from brown seaweeds is partially hydrolyzed and then mixed with other ingredients for use as a dietary supplement in beverage, capsule, or tablet form. The fucoidan is partially hydrolyzed with acid and heat. The partially hydrolyzed fucoidan can also be sulfonated. Other ingredients that can be included in the dietary supplement include high-ORAC-value antioxidants, minerals, pepper extract, flavoring agents, coloring agents, and preservatives. The compositions can be in the form of beverages, tablets, capsules, powders, and the like.

1 Claim, No Drawings

U.S. PATENT DOCUMENTS

| | | | |
|---|---|---|---|
| 6,521,240 | B1 | 2/2003 | Minerath |
| 6,573,250 | B2 | 6/2003 | Umeda et al. |
| 6,589,537 | B2 | 7/2003 | Harbeck |
| 6,602,869 | B1 | 8/2003 | Galey |
| 6,616,950 | B2 | 9/2003 | Pushpangadan |
| 6,641,848 | B1 | 11/2003 | Bonte |
| 6,656,903 | B1 | 12/2003 | Sawatzki |
| 6,673,755 | B2 | 1/2004 | Wei |
| 6,693,209 | B2 | 2/2004 | Van Es et al. |
| 6,703,027 | B2 | 3/2004 | Kurosawa |
| 6,730,333 | B1 | 5/2004 | Garrity |
| 6,812,220 | B2 | 11/2004 | Jackson et al. |
| 6,863,918 | B2 | 3/2005 | Bindels |
| 6,890,543 | B2 | 5/2005 | Minami |
| 6,896,766 | B2 | 5/2005 | Sarbo |
| 2002/0076431 | A1 | 6/2002 | Umeda |
| 2002/0197352 | A1 | 12/2002 | Portman |
| 2003/0039670 | A1* | 2/2003 | Mizutani et al. ............ 424/401 |
| 2003/0045572 | A1 | 3/2003 | Niyiro |
| 2003/0064958 | A1 | 4/2003 | Jackson et al. |
| 2003/0083209 | A1 | 5/2003 | Moodycliffe |
| 2003/0207004 | A1 | 11/2003 | Theuer |
| 2004/0043961 | A1 | 3/2004 | Wu |
| 2004/0077523 | A1 | 4/2004 | Ochiai et al. |
| 2004/0180850 | A1 | 9/2004 | Natunen |
| 2004/0242665 | A1 | 12/2004 | Boulle |
| 2005/0013871 | A1 | 1/2005 | Niazi |
| 2005/0015854 | A1 | 1/2005 | Eisenberg |
| 2005/0019356 | A1 | 1/2005 | Bissett |
| 2005/0053713 | A1 | 3/2005 | Birch |
| 2005/0058672 | A1 | 3/2005 | Gupta |
| 2005/0058674 | A1 | 3/2005 | Joseph |
| 2005/0058833 | A1 | 3/2005 | Krzysik |
| 2005/0064070 | A1 | 3/2005 | Liebrecht |
| 2005/0095260 | A1 | 5/2005 | Pardoe |
| 2005/0095320 | A1 | 5/2005 | Botteri |
| 2005/0096295 | A1 | 5/2005 | McMahon |
| 2005/0100636 | A1 | 5/2005 | Botteri |
| 2005/0129708 | A1 | 6/2005 | Fujii et al. |
| 2005/0137175 | A1 | 6/2005 | Bernard |
| 2005/0147732 | A1 | 7/2005 | Schwach-Abdellaoui |
| 2005/0191405 | A1 | 9/2005 | Okos |
| 2005/0192218 | A1 | 9/2005 | Ellis |
| 2005/0214332 | A1 | 9/2005 | Osborne |
| 2005/0214383 | A1 | 9/2005 | Bubnis |
| 2005/0220828 | A1 | 10/2005 | Ullom |
| 2005/0230069 | A1 | 10/2005 | Hilbig |
| 2005/0232876 | A1 | 10/2005 | Minga |
| 2005/0239749 | A1 | 10/2005 | Kambayashi |
| 2005/0244369 | A1 | 11/2005 | Georgiades |
| 2005/0266018 | A1* | 12/2005 | Boreyko et al. ........ 424/195.17 |

FOREIGN PATENT DOCUMENTS

| | | | |
|---|---|---|---|
| EP | 0846422 | | 5/2003 |
| JP | 61111369 | * | 5/1986 |
| JP | 10179157 | * | 7/1998 |
| JP | 3225923 | | 8/2001 |

OTHER PUBLICATIONS

Bank, Ginny and Schauss, Alex, Antoxidant Testing; an ORAC Update. www.nutraceuticalsworld.com, Mar. 2004.

Oliver Starr, Tumeric Phytonutrient Protection for a Variety of Physiological Stresses, VRPs Nutritional News, May/Jun. 1996.

Marilyn Sterling, Proanthocyanidin Power, Nutrition Science News, Jun. 2000.

High-ORAC Foods May SLow Aging, Agricultural Research, Feb. 2005.

Substituting Isosorbides for Phthalates, yet2.com, Dec. 2004.

Novel Plasticizers to Replace Phthalates in PVC or Other Plastics, yet2.com. http://www.yet2.com/app/list/techpak?id=33822&sid=20&abc=0.

Hwan Su Yoon, Ju Yeo Lee, Sung Min Boo, Debashish Bhattacharya, Phylogny of Alariaceae, Laminariaceae, and-Lesoniaceae (RuBisCo Spacer and Nuclear-Encoded ITS Sequence.

Comparisons, Molecular Phylogenitics and Evolution, Nov. 2001, vol. 21, No. 2, pp. 231-243.

Sakait, Ishizukak., Kato, I, Isolation and Characterization of a Fucoidan-Degrading Marine Bacterium, Mar Biotechnical, Sep.-Oct. 2003.

Rita Elkins, Prize Sea Plant of Tonga and the South Pacific—Limu Moui, 2001.

Berteua, Oliver and Mulloy, Barbara, Sulfonated fucans, fresh perspectives; structures, funtions, and biological properties of sulfated fucans and an overview of enzymes active toward this class of polysaccaride, Glycobiology, 2003, vol. 13, No. 6.

Del Bigio, Mr. Yan HJ, Campbell, TM, Peeling, J., Effect of Fucoian Treatment on Collagenase-induced Intracerebral Hemorrhage in rats, 2002 Annual Mtg. and Food Expo., Anaheim, CA.

Shibata, H., Imuro, M., Uhiya N., Kawamori, T., Nagaoka, M., Yeyama S., Hashimoto S., Yokokura T., Sugimura T., Wakabi Ashi K., Preventive Effects of Cladosiphon Fucoidan Against *Helicobacter Pylori* Infection in Mongolian Gerbils, PubMed, Feb. 2003.

A.I., USOV, G.P. Smrinova, N. G. Klochkova, Polysaccharides of Algae: Polysaccharide Composition of Several Brown Algae From Kamchatka, 27 Russian Journal of Bioorganic Chemistry, vol. 27, No. 6, pp. 395-399, 2001.

Berangere, Tissot, Regis, Daniel, Biological Properties of Sulfated Fucans; the Potent Inhibiting Activity of Algal Fucoidan Against the Human Complement System, Glycobiology, 2003 vol. 13, No. 12.

Matou S., Helley D., Chabut D, Bros A Fischer Am, Effect of Fucoidan on Fibroblast Growth Factor-2 induced Angiogenesis in Vitro Elsevier Science, May 15, 2002.

Takara-Takara Kombu Fucoidan (Functional Seaweed Dietary Fiber).

Soeda S, Kozako T. Iwata K., Himeno H., Oversulfated Fucoidan Inhibits the Basic Fibroblast Growth Factor-induced Tube Formation by Human Umbilical Vein Endothelial Cells; Its Possible Mechanism of Action, Department of Biochemistry, Faculty of Pharmaeutical Sciences, Fukuoka University, Jun. 2, 2002.

A Guide to the Seaweed Industry, FAO Fisheries Technical Paper 441, 2003.

Herworld-Back to Basics—http://www.herworld.com/Beauty_report.html.

Desitin—http://www.desitin.com/en/?dsp=21&psp=20.

Desitin Creamy-http://www.desitin.com/en/?dsp=22&psp=20.

Boudreauxs Butt Paste—http://www.skinstore.com/store/product.asp?catID=422&prodID=514.

Johnson's Baby Oil—http://www.johnsonsbaby.com/products/oil/baby-oil.

Johnson's Creamy Baby Oil-http://www.johnsonsbaby.com/products/oil/creamy-baby-oil.

Johnson' Baby Oil Gel with Aloe Vera and Vitamin E-http://www.johnsonsbady.com/products/oil/baby-oil-with-aloe.

Pediatric Products Similac Advance—http://rpdcon40.ross.com/pn/PediatricProducts.NSF/0/706d4b6080c6E7C085256BA30052E1D1?OpenDocument.

Marquardt, Thorsten; Luhn, Kerstin; Srikrishna, Geetha; Freeze, Hudson H; Harms, Erik; Vestweber, Dietmar Correction of Lukocyte Adhesion Deficiency Type II With Oral Fucose-Blood vol. 94, No. 12, Dec. 15, 1999 pp. 3976-3985.

Russian Adaptogens: Health Secrets Revealed—http://members.tripod.com/macyuen-ivil/id13.html (Dec. 2004).

Polysaccharide Found in the Seaweed Kombu, U-Foucoidan, Discovered to Cause Cancer Cells to self Destruct (Jun. 17, 1996).

* cited by examiner

SOLID DOSAGE FORM FOR PROVIDING A DIETARY SUPPLEMENT

This application is a division of, and claims the benefit of, U.S. application Ser. No. 11/083,826 filed on 18 Mar. 2005 by Thomas E. Mower for "Fuoidan Compositions and Methods for Dietary and Nutritional Supplements," which is herein incorporated by reference, of which application another divisional filed the same day as this application by the same inventor titled "Method of Making a Partially Hydrolyzed Fucoidan Composition".

BACKGROUND OF THE INVENTION

Field of the Invention

This invention relates generally to a solid dosage for providing a dietary supplement. More particularly, the present invention relates a solid dosage form comprising partially hydrolyzed fucoidan.

Fucoidan is a sulfated polysaccharide found in many sea plants and animals and is particularly concentrated in the cell walls of brown algae (*Phaeophyceae*). Fucoidan is a complex carbohydrate polymer composed mostly of sulfated L-fucose residues. These polysaccharides are easily extracted from the cell wall of brown algae with hot water or dilute acid and can account for more than 40% of the dry weight of isolated cell walls. O. Berteau & B. Mulloy, Sulfated fucans, fresh perspectives: structures, functions, and biological properties of sulfated fucans and an overview of enzymes active toward this class of polysaccharide, 13 Glycobiology 29R-40R (2003). Fucoidan structure appears to be linked to algal species, but there is insufficient evidence to establish any systematic correspondence between structure and algal order. High amounts of $\alpha(1\text{-}3)$ and $\alpha(1\text{-}4)$ glycosidic bonds occur in fucoidans from *Ascophyllum nodosum*. A disaccharide repeating unit of alternating $\alpha(1\text{-}3)$ and $\alpha(1\text{-}4)$ bonds represents the most abundant structural feature of fucoidans from both *A. nodosum* and *Fucus vesiculosus*. Sulfate residues are found mainly in position 4. Further heterogeneity is added by the presence of acetyl groups coupled to oxygen atoms and branches, which are present in all the plant fucoidans.

Fucoidan-containing seaweeds have been eaten and used medicinally for at least 3000 years in Tonga and at least 2000 years in China. An enormous amount of research has been reported in the modern scientific literature, where more than 500 studies are referenced in a PubMed search for fucoidan.

The physiological properties of fucoidans in the algae appear to be a role in cell wall organization and possibly in cross-linking of alginate and cellulose and morphogenesis of algal embryos. Fucoidans also have a wide spectrum of activity in biological systems. They have anticoagulant and antithrombotic activity, act on the inflammation and immune systems, have antiproliferative and antiadhesive effects on cells, and protect cells from viral infection.

Further, fucoidan has numerous beneficial functions that heal and strengthen different systems of the body, including anti-viral, anti-inflammatory, anti-coagulant, and anti-tumor properties. A. I. Usov et al., Polysaccharides of Algae: Polysaccharide Composition of Several Brown Algae from Kamchatka, 27 Russian J. Bio. Chem. 395-399 (2001). Fucoidan has been found to build and stimulate the immune system. Research has also indicated that fucoidan reduces allergies, inhibits blood clotting, fights diabetes by controlling blood sugar, prevents ulcers, relieves stomach disorders, reduces inflammation, protects the kidneys by increasing renal blood flow, and detoxifies the body. Fucoidan also helps to reduce and prevent cardiovascular disease by lowering high cholesterol levels and activating enzymes involved in the beta-oxidation of fatty acids.

A Japanese study found that fucoidans enhanced phagocytosis, the process in which white blood cells engulf, kill, digest, and eliminate debris, viruses, and bacteria. An American study reported that fucoidans increased the number of circulating mature white blood cells. An Argentine study and a Japanese study found that fucoidans inhibited viruses, such as herpes simplex type I, from attaching to, penetrating, and replicating in host cells. A Swedish study is among the many that showed fucoidans inhibit inflammation cascades and tissue damage that may lead to allergies. Other studies, such as one in Canada, found that fucoidans block the complement activation process that is believed to play an adverse role in chronic degenerative diseases, such as atherosclerosis, heart attack, and Alzheimer's disease. Two American studies found that fucoidans increase and mobilize stem cells.

Researchers have also determined that fucoidan tends to combat cancer by reducing angiogenesis (blood vessel growth), inhibiting metastasis (spreading of cancer cells to other parts of the body), and promoting death of cancer cells. Certain societies that make brown seaweed part of their diet appear to have remarkably low instances of cancer. For example, the prefecture of Okinawa, where the inhabitants enjoy some of the highest life expectancies in Japan, also happens to have one of the highest per capita consumption rates of fucoidans. It is noteworthy that the cancer death rate in Okinawa is the lowest of all the prefectures in Japan.

Brown seaweed is found in abundance in various ocean areas of the world. One of the purest locations that provides some of the highest yields of fucoidan is in the clear waters surrounding the Tongan islands, where the seaweed is called limu moui. In Japan, hoku kombu (*Laminaria japonica*), is said to be particularly rich in fucoidans and is similar to limu moui. The Japanese also consume at least two other types of brown seaweed-wakame and mozuku (*Cladosiphon* and *Nemacystus*).

Typically, about four percent by weight of Tongan limu moui is fucoidan. There are at least three types of fucoidan polymer molecules found in brown seaweed. U-fucoidan, having about 20 percent glucuronic acid, is particularly active in carrying out cancer cell destruction. F-fucoidan, a polymer of mostly sulfated fucose, and G-fucoidan both tend to induce the production of HGF cells that assist in restoring and repairing damaged cells. All three types of fucoidan also tend to induce the production of agents that strengthen the immune system.

Accordingly, solid dosage forms of fucoidan are needed to benefit from the many advantages mentioned above. Methods of preparation of fucoidan may be used to enhance consumption while not destroying its beneficial effects.

In view of the foregoing, it will be appreciated that providing a fucoidan-containing nutritional supplement would be a significant advancement in the art.

BRIEF SUMMARY OF THE INVENTION

Dietary supplements according to the present invention provide many beneficial effects, among them providing for life extension, anti-aging, and regeneration of cells and tissues, such as muscles and bones; promoting growth factors in the body; promoting high energy, vitality, and youthfulness; preventing blood clots and thrombosis; reducing and preventing inflammation; strengthening the immune system; protecting against viral, bacterial, and other types of infection; preventing tumorigenesis and the spread of cancers; reducing allergies; fighting diabetes by controlling blood sugar; preventing ulcers; relieving stomach disorders; protecting the kidneys by increasing renal blood flow; detoxifing the body; reducing and preventing cardiovascular disease; and activating stem cells.

An illustrative embodiment of the invention comprises a solid dosage form for providing a dietary supplement, the dosage form comprising partially hydrolyzed fucoidan. This solid dosage form illustratively comprises a tablet, capsule, or spray dried or freeze dried powder. The solid dosage form can additionally contain any of the ingredients described above in connection with the liquid forms of the dietary supplement. In addition, the solid dosage forms can contain pharmaceutical necessities useful for the manufacture and compounding thereof.

Another illustrative embodiment of a dietary supplement according to the present invention comprises about 0.5 to about 70 parts by weight of partially hydrolyzed fucoidan and about 30 to about 99.5 parts by weight of water. The partially hydrolyzed fucoidan can be sulfonated or not during the hydrolysis reaction. Sulfonated fucoidan is believed to provide certain benefits to the dietary supplement, such as enhanced properties relating to anti-cancer, antimicrobial, anti-inflammation, life extension, anti-aging, cell and tissue regeneration, and stem cell activation effects. Additional illustrative embodiments further comprise other ingredients, which optionally may be added in any selected combination. For example, a dietary supplement may additionally comprise about 0.5 to about 20 parts by weight of a nutraceutical ingredient having a high ORAC value, such as concentrates of black grapes, red grapes, white grapes, blueberry, acai fruit, raspberry, blackberry, strawberry, plum, orange, cherry, kiwi fruit, currant, elderberry, black currant, cranberry, mangosteen, noni, aronia, wolfberry, proanthocyanidins (such as from grape seed extract), curcuminoids, or mixtures thereof. Further, a dietary supplement may further comprise about 0.01 to about 2 parts by weight of minerals, such as deep sea minerals. Still further, a dietary supplement may further comprise about 0.001 to about 1 parts by weight of pepper extract, such as black pepper or Sichuan pepper extract or mixtures thereof. The fucoidan from which the partially hydrolyzed fucoidan is made can be from Tongan limu moui seaweed or Japanese mozuku or kombu seaweeds, or a mixture of such fucoidans. The dietary supplement can additionally comprise flavoring agents, preservatives, and the like.

Another illustrative dietary supplement according to the present invention comprises about 0.5 to about 70 parts by weight of partially hydrolyzed fucoidan, about 0.5 to about 20 parts by weight of a nutraceutical ingredient having a high ORAC value and about 10 to about 99 parts by weight of water.

Still another illustrative dietary supplement according to the present invention comprises about 0.5 to about 70 parts by weight of partially hydrolyzed fucoidan, about 0.001 to about 1 parts by weight of pepper extract, and about 29 to about 99.5 parts by weight of water.

Yet another illustrative dietary supplement according to the present invention comprises about 0.5 to about 70 parts by weight of partially hydrolyzed, sulfonated fucoidan, about 0.001 to about 1 parts by weight of pepper extract, about 0.5 to about 20 parts by weight of a nutraceutical ingredient having a high ORAC value, and about 9 to about 99.0 parts by weight of water.

DETAILED DESCRIPTION

Before the present fucoidan-containing dietary supplements and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a dietary supplement containing "a partially hydrolyzed fucoidan" includes a mixture of two or more of such partially hydrolyzed fucoidans, reference to "an acid" includes reference to two or more of such acids, and reference to "a preservative" includes reference to a mixture of two or more of such preservatives.

In describing and claiming the present invention, the following terminology will be used in accordance with the definitions set out below.

As used herein, "comprising," "is," "are," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "partially hydrolyzed fucoidan" means fucoidan that has been hydrolyzed into smaller polymers and oligomers, but not so thoroughly hydrolyzed as to result in complete hydrolysis to monosaccharides.

As used herein, "high ORAC value" or similar terms means an ORAC value of at least about 400 per 100 grams of fruit or vegetable. For example, blueberries have an ORAC value of about 2,400 per 100 grams, and the following fruits have ORAC values as shown in parentheses per 100 grams: blackberries (2,036), cranberries (1,750), strawberries (1,540), raspberries (1,220), plums (949), oranges (750), red grapes (739) cherries (670), kiwi fruit (602), and white grapes (446). Other fruits known to have a high ORAC value include black grapes, mangosteen, noni, aronia, wolfberry, and acai, and the like. Further, nutraceutical ingredients known to have high ORAC values include proanthocyanidins, such as from extracts of grape seed and bark of white pine of southern Europe (e.g., pycnogenol, U.S. Pat. No. 4,698,360), and curcuminoids. Oligomeric proanthocyanidins (OPC) are illustrative.

As used herein, "sterilizing" and similar terms means, with respect to nutritional supplements having a pH less than 4.6 and a water activity greater than 0.85, pasteurizing the nutritional supplement and storing at room temperature. With respect to nutritional supplements having a pH greater than 4.6 and a water activity greater than 0.85, "sterilizing" and similar terms mean applying heat such that the nutritional supplement is rendered free of microorganisms capable of reproducing in the nutritional supplement under normal non-refrigerated conditions of storage and distribution.

As used herein, "pasteurization" traditionally means a process named after scientist Louis Pasteur by which every particle of milk is heated to not lower than 62.8° C. (i.e., 145° F.) for not less than 30 minutes and promptly cooled to destroy any harmful bacteria that may be present without affecting flavor and food value. Currently, the most common method of pasteurization in the United States is High Temperature Short Time (HTST) pasteurization, which uses metal plates and hot water to raise temperatures to 71.7° C. (i.e., 161° F.) for not less than 15 seconds, followed by rapid cooling. Ultra Pasteurization (UP) is a process similar to HTST pasteurization, but using higher temperatures and longer times. UP pasteurization results in a product with longer shelf life but still requiring refrigeration of milk, but not of acidified foods or nutritional supplements (pH <4.6). Another method, Ultra High Temperature (UHT) pasteurization, raises the temperature to over 93.3° C. (i.e., 200° F.) for a few seconds, followed by rapid cooling. A UHT-pasteurized product that is packaged aseptically results in a "shelf stable" product that does not require refrigeration until it is opened.

As used herein, "aseptic processing and packaging" and similar terms mean the filling of a sterilized cooled product into pre-sterilized containers, followed by aseptic hermetic sealing, with a pre-sterilized closure, in an atmosphere free of microorganisms.

As used herein, "hermetically sealed container" and similar terms mean a container that is designed and intended to be secure against the entry of microorganisms and thereby to maintain the sterility of its contents after processing.

As used herein, "tablets" are solid dosage forms containing a dietary supplement with or without suitable excipients or diluents and prepared either by compression or molding methods well known in the art. Tablets have been in widespread use since the latter part of the 19$^{th}$ century and their popularity continues. Tablets remain popular as a dosage form because of the advantages afforded both to the manufacturer (e.g., simplicity and economy of preparation, stability, and convenience in packaging, shipping, and dispensing) and the user (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amount of dietary supplement present and the intended method of administration. They are divided into two general classes, (1) compressed tablets, and (2) molded tablets or tablet triturates. In addition to the active or therapeutic ingredient or ingredients, tablets contain a number or inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, flavors, and sweetening agents.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" vary considerably in their chemical structure, ranging from simple esters, alcohols, and aldehydes to carbohydrates and complex volatile oils. Natural and synthetic flavors of almost any desired type are now available.

As used herein, "capsules" are solid dosage forms in which the dietary supplement is enclosed in a hard or soft (including gel caps), soluble container or shell of a suitable polymer, such as gelatin. The soft gelatin capsule was invented by Mothes, a French pharmacist in 1833. During the following year DuBlanc obtained a patent for his soft gelatin capsules. In 1848 Murdock patented the two-piece hard gelatin capsule. The encapsulation of medicinal agents, dietary supplements, and the like remains a popular method of administering agents by the oral route. Capsules are tasteless, easily administered, and easily filled. Some persons find it easier to swallow capsules than tablets, therefore preferring to take this form when possible. This preference has prompted manufacturers to market products in capsule form even though the product has already been produced in tablet form.

As used herein, "pharmaceutical necessities" means substances that are of little or no dietary or therapeutic value, but which are useful in the manufacture and compounding of various dietary supplement preparations. These substances include antioxidants and preservatives; coloring, flavoring, and diluting agents; emulsifying and suspending agents; ointment bases; pharmaceutical solvents; and miscellaneous agents. See, for example, Remington's Pharmaceutical Sciences for a review of what is known in the art concerning pharmaceutical necessities.

As used here, "powders" means a solid dosage form intended to be suspended or dissolved in water or another liquid or mixed with soft foods prior to administration. Powders are typically prepared by spray drying or freeze drying of liquid formulations. Powders are advantageous due to flexibility, stability, rapid effect, and ease of administration.

As used herein, "Brix" is a scale for measuring the sugar content of grapes, wine, and the like. Each degree of Brix is equivalent to one gram of sugar per 100 ml of liquid. Thus, an 18 degree Brix sugar solution contains 18% by weight of sugar. Brix also describes the percent of suspended solids in a liquid. Thus, 95 Brix, for example, denotes a liquid that contains 95% by weight of suspended solids. Brix is measured with an optical device called a refractometer. The Brix system of measurement is named for A. F. W. Brix, a $19^{th}$ century German inventor.

The present invention advances prior art dietary supplements by providing a dietary supplement formulated with fucoidan from seaweed, such as limu moui, kombu, or mozuku. The addition of fucoidan to the dietary supplement of the present invention serves to provide significant dietary and nutritional advantages not found in prior art dietary supplements. The fucoidan-enhanced dietary supplement of the present invention provides many beneficial functions, including providing for life extension, anti-aging, and regeneration of cells and tissues, such as muscles and bones; promoting growth factors in the body; promoting high energy, vitality, and youthfulness; maintaining and strengthening the immune system, reducing allergies, inhibiting blood clotting, controlling blood sugar, preventing ulcers, relieving stomach disorders, reducing inflammation, protecting the kidneys, and detoxifying the body. Fucoidan preparations according to the present invention may also help to reduce and prevent cardiovascular disease by lowing cholesterol levels, inhibiting smooth muscle cell proliferation, and activating enzymes involved in the beta-oxidation of fatty acids.

In addition, the fucoidan-enhanced dietary supplement of the present invention fights cancerous tumors and minimizes the visible signs of both biological and environmental aging. That is, the present dietary supplements slow the aging process. assist in regenerating damaged cells and tissues, and promote growth factors in the body. Fucoidan is high in antioxidants that help to fight free radical damage to the body that may lead to cancer. Fucoidan also provides significant benefits to the skin. Fucoidan is high in antioxidants that help to fight free radical damage caused by the sun and other changing environmental conditions and elements.

Brown seaweed grows in many oceans, including off the coasts of Japan and Okinawa, Russian coastal waters, Tonga, and other places. An excellent source of fucoidan is the limu moui sea plant growing in the waters of the Tongan islands. This brown seaweed contains many vitamins, minerals, and other beneficial substances and is particularly rich in fucoidan.

Typically, the brown seaweed grows in long angel hair stems with numerous leaves. The fucoidan ingredient is found in natural compositions on the cell walls of the seaweed, providing a slippery sticky texture that protects the cell walls from the sunlight.

In one embodiment, a kombu-type or mozuku-type seaweed is harvested from the coastal waters of the Tongan islands. These seaweeds are typically manually harvested, including stems and leaves, by divers and cleaned to remove extraneous materials. The seaweed is then usually frozen in large containers and shipped to a processing plant.

In processing, the heavy outer fibers must first be broken down to provide access to the fucoidan component. If frozen, the seaweed material is first thawed, but if not frozen, then the seaweed materia is placed in a mixing vat and shredded, while being hydrolyzed with acids and water. The material can optionally be sulfonated with sulfuric acid to help in breaking down the heavy cell fibers. The mixture is also buffered with citric acid and thoroughly blended to maintain suspension. The material may also be heated at atmospheric or greater than atmospheric pressure while mixing. The resulting puree is tested and maintained at a pH of about 2 to 4 so as to remain acidic, enhancing preservative and stability characteristics.

The hydrogen ion concentration is typically adjusted by adding an acid, according to methods well known in the art. An illustrative acid comprises sulfuric acid, and when sulfuric acid is used, the conditions can be selected such that available reactive groups created by partial hydrolysis of the fucoidan are sulfonated, resulting in a partially hydrolyzed, sulfonated fucoidan composition.

The puree may be used in preparing dietary supplement products. Alternately, the mixture may be refrozen in small containers for later processing.

The present invention provides a dietary supplement beverage formulated with fucoidan compositions from seaweed, such as the limu moui seaweed plant. The fucoidan compositions are present in selected embodiments from about 0.5 to about 70 percent by weight of the total weight of the composition. Other ingredients may include an antioxidant, such a acai fruit and blueberry having a high oxygen radical absorbance capacity (ORAC). Such antioxidants may be present in amounts from about 0 to about 20 percent by weight. Additionally, minerals such as deep sea minerals may be present in an amount from about 0 to about 2 percent by weight, to provide important minerals.

High ORAC Nutraceutical Ingredients

Free radicals are very reactive and highly destructive compounds in the body. Free radicals are products of oxidative deterioration of such substances as polyunsaturated fat. Antioxidants convert free radical into a less reactive and nonharmful chemical form. Antioxidants that can be used in dietary supplements include β-carotene, vitamin E, vitamin C, N-acetyl cysteine, α-lipoic acid, selenium, and the like. Antioxidants having a high ORAC value are particularly desirable. Illustratively, nutraceutical antioxidants of high ORAC value that can be used in the present invention include concentrates of grape (red, black, or white), blueberry, acai fruit, raspberry, blackberry, strawberry, plum, orange, cherry, kiwi fruit, currant, elderberry, black currant, cranberry, mangosteen, noni, aronia, wolfberry, and mixtures thereof. Other high ORAC nutraceutical ingredients include proanthocyanidins, such as oligomeric proanthocyanidins, curcuminoids, and the like.

Minerals

Minerals serve a wide variety of essential physiological functions ranging from structural components of body tissues to essential components of many enzymes and other biological important molecules. Minerals are classified as micronutrients or trace elements on the basis of the amount present in the body. The seven micronutrients (calcium, potassium, sodium, magnesium, phosphorus, sulfur, and chloride) are present in the body in quantities of more than five grams. Trace elements, which include boron, copper, iron, manganese, selenium, and zinc are found in the body in quantities of less than five grams.

Micronutrient Minerals. Calcium is the mineral element believed to be most deficient in the diet in the United States. Calcium intakes in excess of 300 mg per day are difficult to achieve in the absence of milk and dairy products in the diet. This is far below the recommended dietary allowance (RDA) for calcium (1000 mg per day for adults and children ages one to ten, 1200 mg per day for adolescents and pregnant and lactating women, which equates to about four glasses of milk per day). In fact, it has been reported that the mean daily calcium intake for females over age 12 does not exceed 85 percent of the RDA. In addition, during the years of peak bone mass development (18 to 30), more than 66 percent of all U.S. women fail to consume the recommended amounts of calcium on any given day. After age 35, this percentage increases to over 75 percent.

Although the general public is not fully aware of the consequences of inadequate mineral intake over prolonged periods of time, there is considerable scientific evidence that low calcium intake is one of several contributing factors leading to osteoporosis. In addition, the dietary ratio of calcium to phosphorous (Ca:P) relates directly to bone health. A Ca to P ratio of 1:1 to 2:1 is recommended to enhance bone marrowization in humans. Such ratios are difficult to achieve absent an adequate dietary supply of milk and dairy products, or an adequate supply of calcium and other minerals for the lactose-intolerant segment of the population.

Magnesium is the second most plentiful cation of the intracellular fluids. It is essential for the activity of many enzyme systems and plays an important role with regard to neurochemical transmission and muscular excitability. Deficits are accompanied by a variety of structural and functional disturbances. The average 70-kg adult has about 2000 mEq of magnesium in his body. About 50% of this magnesium is found in bone, 45% exists as an intracellular cation, and 5% is in the extracellular fluid. About 30% of the magnesium in the skeleton represents an exchangeable pool present either within the hydration shell or on the crystal surface. Mobilization of the cation from this pool in bone is fairly rapid in children, but not in adults. The larger fraction of magnesium in bone is apparently an integral part of bone crystal.

The average adult in the United States ingests about 20 to 40 mEq of magnesium per day in an ordinary diet, and of this about one third is absorbed from the gastrointestinal tract. The evidence suggests that the bulk of the absorption occurs in the upper small bowel. Absorption is by means of an active process apparently closely related to the transport system for calcium. Ingestion of low amounts of magnesium results in increased absorption of calcium and vice versa.

Magnesium is a cofactor of all enzymes involved in phosphate transfer reactions that utilize adenosine triphosphate (ATP) and other nucleotide triphosphates as substrates. Various phosphatases and pyrophosphatases also represent enzymes from an enormous list that are influenced by this metallic ion.

Magnesium plays a vital role in the reversible association of intracellular particles and in the binding of macromolecules to subcellular organelles. For example, the binding of messenger RNA (mRNA) to ribosomes is magnesium dependent, as is the functional integrity of ribosomal subunits. Certain of the effects of magnesium on the nervous system are similar to those of calcium. An increased concentration of magnesium in the extracellular fluid causes depression of the central nervous system (CNS). Hypomagnesemia causes increased CNS irritability, disorientation, and convulsions. Magnesium also has a direct depressant effect on skeletal muscle. Abnormally low concentrations of magnesium in the extracellular fluid result in increased acetylcholine release and increased muscle excitability that can produce tetany.

Trace Elements. Boron is required by the body in trace amounts for proper metabolism of calcium, magnesium, and phosphorus. Boron helps brain function, healthy bones, and can increase alertness. Boron is also useful for people who want to build muscle. Boron is known to help prevent postmenopausal osteoporosis. Further, a relationship has been shown between a lack of boron in the diet and the chances of developing arthritis. R. E. Newnham, 46 Journal of Applied Nutrition (1994).

Chromium is an important trace element wherein the lack of sufficient chromium in the diet leads to impairment of glucose utilization, however, disturbances in protein and lipid metabolism have also been observed. Impaired glucose utilization occurs in many middle-aged and elderly human beings. In experimental studies, significant numbers of such persons have shown improvement in their glucose utilization after treatment with chromium. Chromium is transported by transferrin in the plasma and competes with iron for binding sites. Chromium as a dietary supplement may produce benefits due to its enhancement of glucose utilization and its possible facilitating the binding of insulin to insulin receptors, which increases its effects on carbohydrate and lipid metabolism. Chromium as a supplement may produce benefits in atherosclerosis, diabetes, rheumatism, and weight control.

Copper is another important trace element in the diet. The most common defect observed in copper-deficient animals is anemia. Other abnormalities include growth depression, skeletal defects, demyelination and degeneration of the nervous system, ataxia, defects in pigmentation and structure of hair or wool, reproductive failure and cardiovascular lesions, including dissecting aneurisms. Several copper-containing metalloproteins have been isolated, including tyrosinase, ascorbic acid oxidase, laccase, cytochrome oxidase, uricase, monoamine oxidase, δ-aminolevulinic acid hydrydase, and dopamine-β-hydroxylase. Copper functions in the absorption and utilization of iron, electron transport, connective tissue metabolism, phospholipid formation, purine metabolism, and development of the nervous system. Ferroxidase I (ceruloplasmin), a copper-containing enzyme, effects the oxidation of Fe(II) to Fe(III), a required step for mobilization of stored iron. A copper-containing enzyme is thought to be responsible for the oxidative deamination of the epsilon amino group of lysine to produce desmosine and isodesmosine, the cross-links of elastin. In copper-deficient animals the arterial elastin is weaker and dissecting aneurisms may occur.

Iodine is important for the production of thyroid hormones, which regulate cellular oxidation. The iodine-deficiency disease is goiter. In iodine-deficient young, growth is depressed and sexual development is delayed, the skin and hair are typically rough, and the hair becomes thin. Cretinism, feeblemindedness, and deaf-mutism occur in a severe deficiency. There is reproductive failure in females and decreased fertility in males that lack sufficient iodine in the diet.

Iron is an essential component of several important metalloproteins. These include hemoglobin, myoglobin, and many oxidation-reduction enzymes. In iron deficiency, there may be reduced concentrations of some of the iron-containing enzymes, such as cytochrome c in liver, kidney, and skeletal muscle, and succinic dehydrogenase in the kidney and heart.

Manganese plays a role in the synthesis of GAGs, collagen, and glycoproteins, which are important constituents of cartilage and bone. Manganese is required for enzyme activity of glycosyltransferases. This family of enzymes is responsible for linking sugars together into GAGs, adding sugars to other glycoproteins, adding sulfate to aminosugars, converting sugars to other modified sugars, and adding sugars to lipids. These functions are manifested as GAG synthesis (hyaluronic acid, chondroitin sulfate, karatan sulfate, heparin sulfate, and dermatin sulfate, among others), collagen synthesis, and function of many other glycoproteins and glycolipids. GAGs and collagen are chief structural elements for all connective tissues. Their synthesis is essential for proper maintenance and repair of connective tissues.

Manganese deficiencies in humans and animals lead to abnormal bone growth, swollen and enlarged joints, and slipped tendons. In humans, manganese deficiencies are associated with bone loss, arthritis, and impaired glucose utilization. Levels of all GAGs are decreased in connective tissues during manganese deficiencies, with chondroitin sulfates being most depleted. Manganese-deficient organisms quickly normalize GAG and collagen synthesis when manganese is provided.

Manganese is also required for activity of manganese superoxide dismutase (MnSOD), which is present only in mitochondria. Manganese deficiency decreases the activity of MnSOD and may lead to mitochondrial dysfunction, manifested as decreased cellular functions. Manganese is required for the conversion of mevalonic acid to squalene. Pyruvate carboxylase is a manganese metalloenzyme, repressible by insulin, important in the citric acid cycle for the oxidation of carbohydrates, lipids, and proteins, as well as in the synthesis of glucose and lipids.

Molybdenum is an essential mineral found in highest concentrations in the liver, kidneys, skin, and bones. This mineral is required by the body to properly metabolize nitrogen. It is also a vital component of the enzyme xanthine oxidase, which is required to convert purines to uric acid, a normal byproduct of metabolism. Molybdenum also supports the body's storage of iron and other cellular functions such as growth. A deficiency of molybdenum is associated with mouth and gum disorders and cancer. A diet high in refined and processed foods can lead to a deficiency of molybdenum, resulting in anemia, loss of appetite and weight, and stunted growth in animals. While these deficiencies have not been observed directly in humans, it is known that a molybdenum deficiency can lead to impotence in older males.

Selenium is an essential trace element that functions as a component of enzymes involved in protection against antioxidants and thyroid hormone metabolism. In several intra- and extra-cellular glutathione peroxidases and iodothyronine 5'-deiodinases, selenium is located at the active centers as the selenoamino acid, selenocysteine (SeCYS). At least two other proteins of unknown function also contain SeCYS. Although SeCYS is an important dietary form, it is not directly incorporated into these specific selenium-proteins; instead, a co-translational process yields tRNA-bound SeCYS. In contrast, selenium as seleno-methionine is incorporated non-specifically into many proteins, as it competes with methionine in general protein synthesis. Therefore, tissues often contain both specific, as well as the nonspecific, selenium-containing proteins when both SeCYS and selenomethionine are consumed, as found in many foods. Selenium is a major antioxidant nutrient and is involved in protecting cell membranes and preventing free radical generation, thereby decreasing the risk of cancer and disease of the heart and blood vessels. Medical surveys show that increased selenium intake decreases the risk of breast, colon, lung and prostate cancer. Selenium also preserves tissue elasticity; slows down the aging and hardening of tissues through oxidation; and helps in the treatment and prevention of dandruff. Recent research has shown antitumorigenic effects of high levels of selenium in the diets of several animal models.

Vanadium is an essential nutrient beneficial for thyroid hormone metabolism. The daily requirement necessary to prevent a deficiency is about 10 to 20 micrograms a day. Vanadium deficiency can lead to slow growth, defective bones, and altered lipid metabolism. Vanadium exerts an insulin-like effect in some respects, and there has been a considerable amount of research on vanadium and diabetes. In insulin dependent diabetics, vanadium has been found to reduce the amount of insulin required to manage the disease, and in non-insulin dependent diabetics, vanadium has been known to control the condition altogether. Research has shown that supplementation with vanadium leads to an increase in glucose transport into cells, which suggests that vanadium supplementation of the diet improves glucose metabolism and may aid in preventing diabetes.

Zinc is known to occur in many important metalloenzymes. These include carbonic anhydrase, carboxypeptidases A and B, alcohol dehydrogenase, glutamic dehydrogenase, D-glyceraldehyde-3-phosphate dehydrogenase, lactic dehydrogenase, malic dehydrogenase, alkaline phosphatase, and aldolase. Impaired synthesis of nucleic acids and proteins has been observed in zinc deficiency. There is also evidence that zinc may be involved in the secretion of insulin and in the function of the hormone.

According to the present invention, minerals can be provided as inorganic compounds, such as chlorides, sulfates, and the like. In addition, some minerals can be provided in more bioavailable forms, such as amino acid chelates, which are well known in the art. U.S. Pat. No. 5,292,538. Examples of minerals that can be provided as amino acid chelates include calcium, magnesium, manganese, zinc, iron, boron, copper, molybdenum, and chromium. Still further, minerals can be provided as deep sea minerals.

Additional elements of the presently disclosed compositions may include fruit flavorings and colorings, such as grape and raspberry in small amounts. Sweeteners, such as momordica fruit may also be included. Components to enhance absorption into the body, such as black or Sichuan pepper extracts may be added. Preservatives, such as sodium benzoate or potassium sorbate may also be included. Substantially pure water, such as deionized water, is also an important ingredient of the liquid mixture.

In one embodiment, the dietary supplement may be provided as a nutritional drink or beverage. The supplement may also be dried into a powder and provided as a freeze dried or spray dried powder, capsule, or tablet. An illustrative beverage supplement is now described in greater detail.

Starting with the fucoidan-containing puree described above, juices or concentrates to provide a high oxygen radical absorbance capacity (ORAC), such as acai fruit, grape, and blueberry are added. Also, fruit flavoring and colorings, such as grape and raspberry; minerals, such as deep sea minerals; sweeteners, such as momordica fruit; pepper for flavor enhancement and to enhance absorption into the body, such as black pepper; preservative, such as sodium benzoate or potassium sorbate; and deionized water are added to the mixture. Next, the mixture is sterilized by pasteurization or other heating techniques. Although pasteurization (at least 87.8° C. or 190° F.) effectively eliminates pathogenic microorganisms, sterilization at higher temperatures maybe needed to eliminate all microorganisms.

In achieving the necessary sterilization, two different sterilization processes are typically used. Using the HTST (high temperature short time) process, the mixture may be raised to about 85° C. (185° F.) for about 20-30 seconds. Alternately, the ultra-high temperature (UHT) process involves raising the temperature of the mixture to about 140.6° C. (285° F.) for about 4-6 seconds. In either process, immediately after the heating step, the temperature is rapidly lowered to at least ambient temperatures of about 21.1-26.7° C. (70-80° F.). Alternately, the mixture may be chilled down to about 4.4° C. (40° F.).

Heating of the mixture may be accomplished by direct or indirect heating. For example, the mixture may be heated by direct contact with steam or indirectly by a selected type of heat exchanger.

The sterilized blend may then be poured into containers, using a hot-fill or cold-fill method. In the hot-fill process, the product is first heated to temperatures for pasteurization, HTST, or UHT. Then it is poured into containers at elevated temperatures to kill any microorganisms inside the container. The use of preservatives, such as sodium benzoate and potassium sorbate are normally used. The pH is usually maintained below 4.4, possibly using acids such as lemon juice or vinegar. After filling, the bottles may be cooled slowly by a water mist. Filling of containers is done by aseptic processing and packaging methods, which are well known in the art.

In the cold-fill process, after pasteurization or sterilization temperatures are reached, the product is immediately cooled to about room temperature prior to bottling, using aseptic processing and packaging techniques. Immediate cooling allows less vitamin degradation and variations in flavor that may be found in the hot-fill process. Thus, in cold-fill processing the flavor may be cleaner and fresher. Preservatives are usually included to control the growth of yeast, molds, and bacteria.

The cold-fill process is compatible with use of high-density polyethylene (HDPE) or polyethylene terephthalate (PET) bottling, so as to not compromise the integrity of the bottle structure. The bottles may be 500 ml bottles, capable of containing about 660 grams per bottle. The size would provide sufficient beverage for 30 days, if a recommended dosage is about 22 grams per day.

Solid dosage forms according to the present invention can be made in the form of powders, tablets, and capsules according to methods well known in the art. For example, powders can be made by drying the fucoidan preparation, and then mixing the dried fucoidan with other dried ingredients. Alternatively, the fucoidan preparation can be mixed with other ingredients, and then the mixture is dried into a powder. Illustrative methods of drying include spray drying and freeze drying. The powder can then be ingested by suspending or dissolving it in a liquid and drinking the resulting suspension or solution. Illustrative liquids that can be used for this purpose include water, juice, and the like. The powder can also be compressed into tablets or loaded into capsules. Tablets or capsules are typically swallowed with water or other liquid. Liquid dietary supplements can also be encapsulated and taken in such a solid dosage form.

EXAMPLES

The following are examples of the preparation of seaweed to provide a fucoidan puree for use in dietary supplements, and dietary supplement formulations prepared from the fucoidan puree. These examples are merely illustrative and are not meant to be limiting in any way.

The present invention may be embodied in other specific forms without departing from its spirit or essential characteristics. The described embodiments are to be considered in all respects only as illustrative and not restrictive. The scope of the invention is, therefore, indicated by the appended claims, rather than by the description or examples. All changes that come within the meaning and range of equivalency of the claims are to be embraced within their scope.

Example 1

Preparation of Fucoidan Puree Composition

Tongan limu moui seaweed was manually harvested, cleaned to remove extraneous material, frozen, and shipped to a processing plant. At the plant, the frozen seaweed was thawed, weighed, and placed in a stainless steel mixer with aqueous buffer and optionally sulfuric acid according to any of the sets of conditions set out in Table 1. The ingredients were then mixed at 50-75 rpm with a medium shear mixer (propeller type). While mixing, the mixture was heated to 37° C. to 95° C. for a selected period of time (usually 5 min to 8 hr). At that point, heating was discontinued, but mixing was continued for 0.5-10 hours to dissipate heat and micronize the seaweed strands. The cooled mixture was then filtered to remove insoluble material, and the filtrate was covered and mixed at room temperature for about 4-72 hours. The pH of the resulting puree was determined to be about pH 2.0 to 4.0, and refractometry typically showed a Brix value of 2-4. The puree comprising partially hydrolyzed fucoidan was then frozen and stored. If sulfuric acid was added during hydrolysis, the partially hydrolyzed fucoidan was sulfonated.

TABLE 1

|  | Trial I | Trial II | Trial III | Trial IV | Trial V | Trial VI | Trial VII |
|---|---|---|---|---|---|---|---|
| pH | 2.0-2.4 | 2.2-2.5 | 2.4-2-7 | 2.6-3.0 | 2.9-3.2 | 3.2-3.6 | 3.6-4.0 |
| sulfuric acid | — | 0.01 N | — | 0.001 N | 0.004 N | — | 0.001 |
| seaweed | 20 wt % | 10 wt % | 25 wt % | 40 wt % | 33 wt % | 15 wt % | 42 wt % |
| temp | 37 C. | 42 C. | 50 C. | 60 C. | 75 C. | 80 C. | 95 C. |
| heating time | 5 hr | 4 hr | 4 hr | 3 hr | 35 min | 20 min | 15 min |
| filtrate mixing | 24 hr, 37 C. | 16 hr, 37 C. | 72 hr, 22 C. | 24 hr, 22 C. | 48 hr, 22 C. | 36 hr, 22 C. | 8 hr, 22 C. |

Example 2

Preparation of Fucoidan Beverage

Fucoidan puree prepared according to the procedure of Example 1 was thawed and then mixed with other ingredients according to the present invention as set out in Tables 2 and 3, where amounts are in parts by weight. These ingredients were blended thoroughly and then sterilized and bottled in by aseptic processing and packaging methods according to any of the conditions set out in Table 4.

TABLE 2

| | Formulation No. 1 | Formulation No. 2 | Formulation No. 3 | Formulation No. 4 | Formulation No. 5 | Formulation No. 6 |
|---|---|---|---|---|---|---|
| fucoidan | 20 | 25 | 30 | 35 | 40 | 45 |
| water | 80 | 75 | 64 | 64.2 | 54.63 | 45.62 |
| grape | | | 6 | | | |
| blueberry | | | | | | 4 |
| acai | | | | 0.5 | | |
| raspberry | | | | | 2.5 | |
| blackberry | | | | | 1.5 | |
| strawberry | | | | | 0.5 | |
| plum | | | | | | |
| orange | | | | | | |
| cherry | | | | | | 4 |
| kiwi | | | | | | |
| currant | | | | | | 1 |
| elderberry | | | | | | |
| black currant | | | | | | |
| cranberry | | | | | | |
| deep sea minerals | | | | | 0.5 | 0.2 |
| momordica | | | | 0.2 | 0.25 | 0.1 |
| sodium benzoate | | | | 0.08 | | 0.05 |
| potassium sorbate | | | | | 0.1 | |
| black pepper | | 0.05 | | | 0.01 | 0.02 |
| Sichuan pepper | | | 0.02 | | | 0.03 |

TABLE 3

| | Formulation No. 7 | Formulation No. 8 | Formulation No. 9 | Formulation No. 10 | Formulation No. 11 | Formulation No. 12 |
|---|---|---|---|---|---|---|
| fucoidan | 0.5 | 8 | 13 | 17 | 19 | 22 |
| water | 86.17 | 85.06 | 83.63 | 76.65 | 72.72 | 69.67 |
| grape | | | 2 | | 5.7 | 5.5 |
| blueberry | | | | 4.2 | | 1.5 |
| acai | | | 0.5 | 0.1 | 0.3 | 0.5 |
| raspberry | | | | | 0.3 | 0.3 |
| blackberry | | | | | 0.1 | |
| strawberry | | | | 1 | 0.8 | |
| plum | | 3.5 | | | | |
| orange | 10 | | | | | |
| cherry | | | | | | |
| kiwi | 3 | | | | 0.4 | |
| currant | | | | | | |
| elderberry | | | 0.3 | | | |
| black currant | | | | 0.5 | | |
| cranberry | | 2.4 | | | | |
| deep sea minerals | | 0.33 | 0.4 | 0.23 | 0.29 | 0.31 |
| momordica | 0.12 | 0.5 | | | 0.17 | 0.16 |
| sodium benzoate | 0.12 | | 0.15 | 0.18 | 0.16 | 0.06 |
| potassium sorbate | 0.08 | 0.2 | | | 0.04 | 0.11 |
| black pepper | 0.005 | 0.01 | | 0.14 | | 0.01 |
| Sichuan pepper | 0.005 | | 0.02 | | 0.015 | |

TABLE 4

| Condition No. | Sterilization | Bottling |
|---|---|---|
| I | 62.8° C., 30 min | hot fill |
| II | 71.7° C., 15 sec | hot fill |
| III | 93.3° C., 10 sec | hot fill |
| IV | 96.0° C., 10 sec | hot fill |
| V | 62.8° C., 30 min | cold fill |
| VI | 140.6° C., 6 sec | cold fill |

Example 3

About 70 parts by weight of fucoidan puree prepared according to the procedure of Example 1 is mixed with about 99 parts by weight of distilled water, about 20 parts by weight of Concord grape extract, about 2 parts by weight of deep sea minerals, about 1 part by weight of momordica, and about 1 part by weight of black pepper extract. The resulting mixture is spray dried into a powder and packaged for storage and distribution.

Example 4

The procedure of Example 3 is followed except that the powder is encapsulated in gelatin capsules.

Example 5

The procedure of Example 3 is followed except that the powder is mixed with selected amounts of diluents, binders, lubricants, disintegrators, colors, flavors, and sweetening agents and then compressed into tablets.

What is claimed is:

1. A solid dosage form for providing a dietary supplement, the dosage form consisting of partially hydrolyzed fucoidan, plum concentrate, grape concentrate, black currant concentrate, blueberry concentrate, raspberry concentrate, black pepper extract, Sichuan pepper extract, minerals, flavoring agent, and sweetener.

* * * * *